(12) United States Patent
Wu et al.

(10) Patent No.: US 10,888,556 B2
(45) Date of Patent: Jan. 12, 2021

(54) METHOD FOR TREATING MYOPIA WITH AN NSAID AND AN ANTI-MUSCARINIC AGENT

(71) Applicants: KAOHSIUNG CHANG GUNG MEMORIAL HOSPITAL, Kaohsiung (TW); Philip Wu, Richmond Hill, NY (US)

(72) Inventors: Pei-Chang Wu, Kaohsiung (TW); Chia-Ling Tsai, Kaohsiung (TW); Chueh-Tan Chen, Kaohsiung (TW)

(73) Assignees: Kaohsiung Chang Gung Memorial Hospital, Kaohsiung (TW); Philip Wu, Richmond Hill, NY (US)

( * ) Notice: Subject to any disclaimer, the term of this patent is extended or adjusted under 35 U.S.C. 154(b) by 0 days.

(21) Appl. No.: 16/701,707

(22) Filed: Dec. 3, 2019

(65) Prior Publication Data

US 2020/0113890 A1 Apr. 16, 2020

Related U.S. Application Data

(62) Division of application No. 15/958,440, filed on Apr. 20, 2018, now Pat. No. 10,548,887, which is a division of application No. 14/787,051, filed as application No. PCT/US2014/036810 on May 5, 2014, now abandoned.

(60) Provisional application No. 61/819,709, filed on May 6, 2013.

(51) Int. Cl.

| | |
|---|---|
| *A61K 31/407* | (2006.01) |
| *A61K 31/46* | (2006.01) |
| *A61P 27/10* | (2006.01) |
| *A61K 45/06* | (2006.01) |
| *A61K 31/165* | (2006.01) |
| *A61K 31/192* | (2006.01) |
| *A61K 31/196* | (2006.01) |
| *A61K 31/405* | (2006.01) |

(52) U.S. Cl.
CPC ............ *A61K 31/46* (2013.01); *A61K 31/165* (2013.01); *A61K 31/192* (2013.01); *A61K 31/196* (2013.01); *A61K 31/405* (2013.01); *A61K 31/407* (2013.01); *A61K 45/06* (2013.01); *A61P 27/10* (2018.01)

(58) Field of Classification Search
CPC ........ A61K 31/46; A61K 31/407; A61P 27/10
See application file for complete search history.

(56) References Cited

U.S. PATENT DOCUMENTS

2007/0254914 A1 11/2007 Wu et al.
2013/0065869 A1 3/2013 Demopulos et al.

FOREIGN PATENT DOCUMENTS

| CA | 2582374 A1 | 4/2006 |
|---|---|---|
| CA | 2697580 A1 | 4/2009 |
| CA | 2809407 A1 | 9/2013 |
| CN | 1651090 A | 8/2005 |
| EP | 0465234 A1 | 1/1992 |
| EP | 2693259 A1 | 2/2014 |
| JP | 2000026313 A | 1/2000 |
| WO | 0195913 A1 | 12/2001 |
| WO | 2009105534 A2 | 8/2009 |
| WO | 2013166408 A1 | 11/2013 |
| WO | 2013177170 A2 | 11/2013 |

OTHER PUBLICATIONS

Maca et al. (American Journal of Ophthalmology, 149, 777-784, May 2010) (Year: 2010).
Solomon et al., "Topical ketorolac tromethamine 0.5% ophthalmic solution in ocular inflammation after cataract surgery," Ophthamology, 108, pp. 331-337, 2001, abstract only.
Lee et al., "Prevention of Myopia Progression with 0.05% Atropine Solution," Journal of Ocular Pharmacology and Therapeutics, Feb. 1, 2006, vol. 22, pp. 41-46.
International Search Report and Written Opinion issued in corresponding Int'l Application No. PCT/US2014/036810 dated Oct. 7, 2014.
Jin et al., "Effects of prostaglandins on form deprivation myopia in the chick," Acta Ophthalmol. Scand. 2000, 78, pp. 495-500.
Search Report dated Jul. 4, 2016, issued by the IPO of Singapore in related Singapore Application No. 11201508453Y (2 pages).
Written Opinion dated Aug. 26, 2016, issued by the IPO of Singapore in related Singapore Application No. 11201508453Y (8 pages).
Diether et al., "Effects of intravitreally and intraperitionally injected atropine on two types of experimental myopia in chicken," Experimental Eye Research, 84 (2007), pp. 266-274 (10 pages).
Office Action issued in corresponding Japanese Application No. 2016512991 dated Oct. 18, 2016 (7 pages).
Office Action issued in corresponding Canadian Application No. 2,911,298 dated Nov. 16, 2016 (4 pages).
Extended European Search Report issued in corresponding European Application No. 14794664.4 dated Nov. 30, 2016 (6 pages).
Office Action issued in corresponding TW Application No. 105126589 dated Jul. 25, 2017 (6 pages).
http://grbsearch.stpi.narl.org.tw/search/planDetail?id=2630638&docid=0 "Chondrogenesis in Scleral Stem/Progenitor Cells and Its Association with Deprivated Myopia in Mice," 2012 (1 page).

(Continued)

*Primary Examiner* — Theodore R. West
(74) *Attorney, Agent, or Firm* — Pilloff Passino & Cosenza LLP; Sean A. Passino; Rachel K. Pilloff

(57) ABSTRACT

Pharmaceutical compositions containing a combination of anti-chondrogenesis agents are disclosed. Methods of reducing scleral chondrogensis, reducing one or more ocular chondrogenic proteins, reducing inflammation induced chondrogensis and treating myopia by administering an effective amount of one or more anti-chondrogensis agents are also provided. The pharmaceutical compositions are useful for treating myopia.

20 Claims, 9 Drawing Sheets

Specification includes a Sequence Listing.

(56) References Cited

OTHER PUBLICATIONS

Pountos et al., "NSAIDS inhibit in vitro MSC chondrogenesis but not osteogenesis: implications for mechanism of bone formation inhibition in man," J Cell Mal Med., Mar. 2011, (2 pages).
Takakuda et al., "Factors for Bone Regeneration"; The Journal of Stomatological Society, 2003, p. 50, vol. 70, Issue 1, 2 pages, Japan.
Zhu et al., "Regulation Effects of the retinal neurotransmitters on form-deprivation myopia"; Rec Adv Ophthalmol, Apr. 2, 2003, pp. 138-141, vol. 23, No. 2.

SEQUENCE LISTING

<160> NUMBER OF SEQ ID NOS: 16

<210> SEQ ID NO 1
<211> LENGTH: 91
<212> TYPE: DNA
<213> ORGANISM: Homo sapiens
<220> FEATURE:
<223> OTHER INFORMATION: miR-449a

<400> SEQUENCE: 1
ctgtgtgtga tgagctggca gtgtattgtt agctggttga atatgtgaat ggcatcggct    60
aacatgcaac tgctgtctta ttgcatatac a                                  91

<210> SEQ ID NO 2
<211> LENGTH: 155
<212> TYPE: PRT
<213> ORGANISM: Homo sapiens
<220> FEATURE:
<223> OTHER INFORMATION: basic fibroblast growth factor(bFGF)

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 3
<211> LENGTH: 27
<212> TYPE: PRT
<213> ORGANISM: Homo sapiens
<220> FEATURE:
<223> OTHER INFORMATION: parathyroid hormone-like peptide

<400> SEQUENCE: 3

Thr Ala Leu Leu Trp Gly Leu Lys Lys Lys Gly Lys Gln Gln Lys
1               5                   10                  15

Asn Thr Ser Tyr Ala Thr Asn Asp Leu Ile Ile
            20                  25

<210> SEQ ID NO 4
<211> LENGTH: 390
<212> TYPE: PRT
<213> ORGANISM: Homo sapiens
<220> FEATURE:
<223> OTHER INFORMATION: Transforming growth factor beta-1 (TGF-beta-1)

<400> SEQUENCE: 4

```
Met Pro Pro Ser Gly Leu Arg Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Ile Glu Ala
                35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
                100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
        260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
        370                 375                 380

Arg Ser Cys Lys Cys Ser
385                 390
```

```
<210> SEQ ID NO 5
<211> LENGTH: 413
<212> TYPE: PRT
<213> ORGANISM: Homo sapiens
<220> FEATURE:
<223> OTHER INFORMATION: Transforming growth factor beta-2 (TGF-beta-2)

<400> SEQUENCE: 5

Met His Tyr Cys Val Leu Ser Ala Phe Leu Ile Leu His Leu Val Thr
  1               5                  10                  15

Val Ala Leu Ser Leu Ser Thr Cys Ser Thr Leu Asp Met Asp Gln Phe
             20                  25                  30

Met Arg Lys Arg Ile Glu Ala Ile Arg Gly Gln Ile Leu Ser Lys Leu
         35                  40                  45

Lys Leu Thr Ser Pro Pro Glu Asp Tyr Pro Glu Pro Glu Glu Val Pro
 50                  55                  60

Pro Glu Val Ile Ser Ile Tyr Asn Ser Thr Arg Asp Leu Leu Gln Glu
 65                  70                  75                  80

Lys Ala Ser Arg Arg Ala Ala Ala Cys Glu Arg Glu Arg Ser Asp Glu
                 85                  90                  95

Glu Tyr Tyr Ala Lys Glu Val Tyr Lys Ile Asp Met Pro Pro Phe Phe
            100                 105                 110

Pro Ser Glu Ala Ile Pro Pro Thr Phe Tyr Arg Pro Tyr Phe Arg Ile
        115                 120                 125

Val Arg Phe Asp Val Ser Ala Met Glu Lys Asn Ala Ser Asn Leu Val
130                 135                 140

Lys Ala Glu Phe Arg Val Phe Arg Leu Gln Asn Pro Lys Ala Arg Val
145                 150                 155                 160

Pro Glu Gln Arg Ile Glu Leu Tyr Gln Ile Leu Lys Ser Lys Asp Leu
                165                 170                 175

Thr Ser Pro Thr Gln Arg Tyr Ile Asp Ser Lys Val Val Lys Thr Arg
            180                 185                 190

Ala Glu Gly Glu Trp Leu Ser Phe Asp Val Thr Asp Ala Val His Glu
        195                 200                 205

Trp Leu His His Lys Asp Arg Asn Leu Gly Phe Lys Ile Ser Leu His
210                 215                 220

Cys Pro Cys Cys Thr Phe Val Pro Ser Asn Asn Tyr Ile Ile Pro Asn
225                 230                 235                 240

Lys Ser Glu Glu Leu Glu Ala Arg Phe Ala Gly Ile Asp Gly Thr Ser
                245                 250                 255

Thr Tyr Thr Ser Gly Asp Gln Lys Thr Ile Lys Ser Thr Arg Lys Lys
            260                 265                 270

Asn Ser Gly Lys Thr Pro His Leu Leu Leu Met Leu Leu Pro Ser Tyr
        275                 280                 285

Arg Leu Glu Ser Gln Gln Thr Asn Arg Arg Lys Lys Arg Ala Leu Asp
290                 295                 300

Ala Ala Tyr Cys Phe Arg Asn Val Gln Asp Asn Cys Cys Leu Arg Pro
305                 310                 315                 320

Leu Tyr Ile Asp Phe Lys Arg Asp Leu Gly Trp Lys Trp Ile His Glu
                325                 330                 335

Pro Lys Gly Tyr Asn Ala Asn Phe Cys Ala Gly Ala Cys Pro Tyr Leu
            340                 345                 350

Trp Ser Ser Asp Thr Gln His Ser Arg Val Leu Ser Leu Tyr Asn Thr
        355                 360                 365

Ile Asn Pro Glu Ala Ser Ala Ser Pro Cys Cys Val Ser Gln Asp Leu
```

```
            370                 375                 380
Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
                405                 410

<210> SEQ ID NO 6
<211> LENGTH: 412
<212> TYPE: PRT
<213> ORGANISM: Homo sapiens
<220> FEATURE:
<223> OTHER INFORMATION: Transforming growth factor beta-3 (TGF-beta-3)

<400> SEQUENCE: 6

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
                100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
            290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
```

```
                    325                 330                 335
Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
            355                 360                 365

Asn Pro Glu Ala Ser Ala Ser Pro Cys Cys Val Pro Gln Asp Leu Glu
        370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 7
<211> LENGTH: 377
<212> TYPE: PRT
<213> ORGANISM: Homo sapiens
<220> FEATURE:
<223> OTHER INFORMATION: alpha smooth muscle actin (alpha-SMA)

<400> SEQUENCE: 7

Met Cys Glu Glu Glu Asp Ser Thr Ala Leu Val Cys Asp Asn Gly Ser
1               5                   10                  15

Gly Leu Cys Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Ser Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Ser Leu Glu Lys
225                 230                 235                 240

Ser Tyr Glu Leu Pro Asp Gly Gln Val Ile Thr Ile Gly Asn Glu Arg
                245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
```

```
            275                 280                 285
Ile Asp Ile Arg Lys Asp Leu Tyr Ala Asn Asn Val Leu Ser Gly Gly
    290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
        355                 360                 365

Pro Ser Ile Val His Arg Lys Cys Phe
370                 375

<210> SEQ ID NO 8
<211> LENGTH: 1487
<212> TYPE: PRT
<213> ORGANISM: Homo sapiens
<220> FEATURE:
<223> OTHER INFORMATION: collagen type II protein (Col2)

<400> SEQUENCE: 8

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
                20                  25                  30

Ser Cys Val Gln Asp Gly Gln Arg Tyr Asn Asp Lys Asp Val Trp Lys
            35                  40                  45

Pro Glu Pro Cys Arg Ile Cys Val Cys Asp Thr Gly Thr Val Leu Cys
        50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
```

-continued

```
                260                 265                 270
Gly Ala Arg Gly Phe Pro Gly Thr Pro Gly Leu Pro Gly Val Lys Gly
            275                 280                 285
His Arg Gly Tyr Pro Gly Leu Asp Gly Ala Lys Gly Glu Ala Gly Ala
        290                 295                 300
Pro Gly Val Lys Gly Glu Ser Gly Ser Pro Gly Glu Asn Gly Ser Pro
305                 310                 315                 320
Gly Pro Met Gly Pro Arg Gly Leu Pro Gly Glu Arg Gly Arg Thr Gly
                325                 330                 335
Pro Ala Gly Ala Ala Gly Ala Arg Gly Asn Asp Gly Gln Pro Gly Pro
            340                 345                 350
Ala Gly Pro Pro Gly Pro Val Gly Pro Ala Gly Gly Pro Gly Phe Pro
        355                 360                 365
Gly Ala Pro Gly Ala Lys Gly Glu Ala Gly Pro Thr Gly Ala Arg Gly
        370                 375                 380
Pro Glu Gly Ala Gln Gly Pro Arg Gly Glu Pro Gly Thr Pro Gly Ser
385                 390                 395                 400
Pro Gly Pro Ala Gly Ala Ser Gly Asn Pro Gly Thr Asp Gly Ile Pro
            405                 410                 415
Gly Ala Lys Gly Ser Ala Gly Ala Pro Gly Ile Ala Gly Ala Pro Gly
            420                 425                 430
Phe Pro Gly Pro Arg Gly Pro Pro Gly Pro Gln Gly Ala Thr Gly Pro
        435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
        515                 520                 525
Ala Pro Gly Glu Arg Gly Pro Ser Gly Leu Ala Gly Pro Lys Gly Ala
    530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                565                 570                 575
Pro Ser Gly Ala Pro Gly Glu Asp Gly Arg Pro Gly Pro Pro Gly Pro
            580                 585                 590
Gln Gly Ala Arg Gly Gln Pro Gly Val Met Gly Phe Pro Gly Pro Lys
        595                 600                 605
Gly Ala Asn Gly Glu Pro Gly Lys Ala Gly Glu Lys Gly Leu Pro Gly
        610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
                645                 650                 655
Gly Ala Pro Gly Pro Ser Gly Phe Gln Gly Leu Pro Gly Pro Pro Gly
            660                 665                 670
Pro Pro Gly Glu Gly Gly Lys Pro Gly Asp Gln Gly Val Pro Gly Glu
        675                 680                 685
```

```
Ala Gly Ala Pro Gly Leu Val Gly Pro Arg Gly Glu Arg Gly Phe Pro
    690             695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
                725                 730                 735
Ala Gly Pro Pro Gly Ala Gln Gly Pro Pro Gly Leu Gln Gly Met Pro
            740                 745                 750
Gly Glu Arg Gly Ala Ala Gly Ile Ala Gly Pro Lys Gly Asp Arg Gly
        755                 760                 765
Asp Val Gly Glu Lys Gly Pro Glu Gly Ala Pro Gly Lys Asp Gly Gly
    770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                805                 810                 815
Ala Arg Gly Ala Pro Gly Glu Arg Gly Glu Thr Gly Pro Pro Gly Pro
            820                 825                 830
Ala Gly Phe Ala Gly Pro Pro Gly Ala Asp Gly Gln Pro Gly Ala Lys
        835                 840                 845
Gly Glu Gln Gly Glu Ala Gly Gln Lys Gly Asp Ala Gly Ala Pro Gly
    850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
                885                 890                 895
Gly Phe Pro Gly Ala Ala Gly Arg Val Gly Pro Pro Gly Ser Asn Gly
            900                 905                 910
Asn Pro Gly Pro Pro Gly Pro Pro Gly Pro Ser Gly Lys Asp Gly Pro
        915                 920                 925
Lys Gly Ala Arg Gly Asp Ser Gly Pro Pro Gly Arg Ala Gly Glu Pro
    930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
                965                 970                 975
Ala Gly Gln Arg Gly Ile Val Gly Leu Pro Gly Gln Arg Gly Glu Arg
            980                 985                 990
Gly Phe Pro Gly Leu Pro Gly Pro Ser Gly Glu Pro Gly Lys Gln Gly
        995                 1000                1005
Ala Pro Gly Ala Ser Gly Asp Arg Gly Pro Pro Gly Pro Val Gly
    1010                1015                1020
Pro Pro Gly Leu Thr Gly Pro Ala Gly Glu Pro Gly Arg Glu Gly
    1025                1030                1035
Ser Pro Gly Ala Asp Gly Pro Pro Gly Arg Asp Gly Ala Ala Gly
    1040                1045                1050
Val Lys Gly Asp Arg Gly Glu Thr Gly Ala Val Gly Ala Pro Gly
    1055                1060                1065
Ala Pro Gly Pro Pro Gly Ser Pro Gly Pro Ala Gly Pro Thr Gly
    1070                1075                1080
Lys Gln Gly Asp Arg Gly Glu Ala Gly Ala Gln Gly Pro Met Gly
    1085                1090                1095
```

-continued

```
Pro Ser Gly Pro Ala Gly Ala Arg Gly Ile Gln Gly Pro Gln Gly
    1100                1105                1110

Pro Arg Gly Asp Lys Gly Glu Ala Gly Glu Pro Gly Glu Arg Gly
    1115                1120                1125

Leu Lys Gly His Arg Gly Phe Thr Gly Leu Gln Gly Leu Pro Gly
    1130                1135                1140

Pro Pro Gly Pro Ser Gly Asp Gln Gly Ala Ser Gly Pro Ala Gly
    1145                1150                1155

Pro Ser Gly Pro Arg Gly Pro Pro Gly Pro Val Gly Pro Ser Gly
    1160                1165                1170

Lys Asp Gly Ala Asn Gly Ile Pro Gly Pro Ile Gly Pro Pro Gly
    1175                1180                1185

Pro Arg Gly Arg Ser Gly Glu Thr Gly Pro Ala Gly Pro Pro Gly
    1190                1195                1200

Asn Pro Gly Pro Pro Gly Pro Pro Gly Pro Pro Gly Pro Gly Ile
    1205                1210                1215

Asp Met Ser Ala Phe Ala Gly Leu Gly Pro Arg Glu Lys Gly Pro
    1220                1225                1230

Asp Pro Leu Gln Tyr Met Arg Ala Asp Gln Ala Ala Gly Gly Leu
    1235                1240                1245

Arg Gln His Asp Ala Glu Val Asp Ala Thr Leu Lys Ser Leu Asn
    1250                1255                1260

Asn Gln Ile Glu Ser Ile Arg Ser Pro Glu Gly Ser Arg Lys Asn
    1265                1270                1275

Pro Ala Arg Thr Cys Arg Asp Leu Lys Leu Cys His Pro Glu Trp
    1280                1285                1290

Lys Ser Gly Asp Tyr Trp Ile Asp Pro Asn Gln Gly Cys Thr Leu
    1295                1300                1305

Asp Ala Met Lys Val Phe Cys Asn Met Glu Thr Gly Glu Thr Cys
    1310                1315                1320

Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485
```

```
<210> SEQ ID NO 9
<211> LENGTH: 21
<212> TYPE: DNA
<213> ORGANISM: Artificial Sequence
<220> FEATURE:
<223> OTHER INFORMATION: Alpha-SMA Forward primer

<400> SEQUENCE: 9
atgcctctgg acgtacaact g                                              21

<210> SEQ ID NO 10
<211> LENGTH: 21
<212> TYPE: DNA
<213> ORGANISM: Artificial Sequence
<220> FEATURE:
<223> OTHER INFORMATION: Alpha-SMA Reverse primer

<400> SEQUENCE: 10
cggcagtagt cacgaaggaa t                                              21

<210> SEQ ID NO 11
<211> LENGTH: 20
<212> TYPE: DNA
<213> ORGANISM: Artificial Sequence
<220> FEATURE:
<223> OTHER INFORMATION: Col2 Forward primer

<400> SEQUENCE: 11
gtccttctgg ccctagaggt                                                20

<210> SEQ ID NO 12
<211> LENGTH: 19
<212> TYPE: DNA
<213> ORGANISM: Artificial Sequence
<220> FEATURE:
<223> OTHER INFORMATION: Col2 Reverse primer

<400> SEQUENCE: 12
tgtttctcct gagcgtcca                                                 19

<210> SEQ ID NO 13
<211> LENGTH: 20
<212> TYPE: DNA
<213> ORGANISM: Artificial Sequence
<220> FEATURE:
<223> OTHER INFORMATION: Beta-actin Forward primer

<400> SEQUENCE: 13
cattgctgac aggatgcaga                                                20

<210> SEQ ID NO 14
<211> LENGTH: 20
<212> TYPE: DNA
<213> ORGANISM: Artificial Sequence
<220> FEATURE:
<223> OTHER INFORMATION: Beta-actin Reverse primer

<400> SEQUENCE: 14
ctgatccaca tctgctggaa                                                20

<210> SEQ ID NO 15
<211> LENGTH: 20
<212> TYPE: DNA
<213> ORGANISM: Artificial Sequence
<220> FEATURE:
<223> OTHER INFORMATION: glyceraldehyde 3-phosphate dehydrogenase
      Forward primer
```

```
<400> SEQUENCE: 15
aactttggca ttgtggaagg                                              20

<210> SEQ ID NO 16
<211> LENGTH: 20
<212> TYPE: DNA
<213> ORGANISM: Artificial Sequence
<220> FEATURE:
<223> OTHER INFORMATION: glyceraldehyde 3-phosphate dehydrogenase
      Reverse primer

<400> SEQUENCE: 16
acacattggg ggtaggaaca                                              20
```

METHOD FOR TREATING MYOPIA WITH AN NSAID AND AN ANTI-MUSCARINIC AGENT

CROSS-REFERENCE TO RELATED APPLICATIONS

This application is a Divisional of U.S. patent application Ser. No. 15/958,440, filed 20 Apr. 2018, which is a Divisional of U.S. patent application Ser. No. 14/787,051, filed on 26 Oct. 2015, which is a U.S. National Stage of International Application No. PCT/US2014/36810 filed on 5 May 2014, which claims priority of U.S. Application No. 61/819,709, filed on 6 May 2013, the entire disclosures of all which are hereby incorporated by reference.

TECHNOLOGY FIELD

The present invention relates to pharmaceutical compositions and methods for the treating myopia, inhibiting ocular chondrogenic protein, scleral chondrogenesis and inflammation induced chondrogenesis.

BACKGROUND OF THE INVENTION

Myopia is due to progressive elongation of the eye and stretching of the ocular tissues. It is an important public health issue, as it affects approximately 25% of the U.S. population, and as high as 80% of the population in some Asian countries. Maculopathy of high myopia has become the leading cause of cataract, glaucoma, retinal detachment, myopic retinal degeneration, visual impairment, and untreatable blindness.

Optical and laser surgical corrective techniques have been used to alter the refractive state of the myopic eye. These therapies, however, do not address the abnormal elongation of the eye and thus do not treat pathologic changes of high myopia patients.

There is still a need for a more effective and safe treatment for myopia. The present invention addresses this need.

BRIEF SUMMARY OF THE INVENTION

Pharmaceutical compositions comprising two anti-chondrogenesis agents are provided herein. The pharmaceutical compositions are effective in treating myopia, reducing one or more chondrogenic proteins and reducing scleral chondrogenesis.

Methods for treating myopia, comprising administering an effective amount of non-steroidal anti-inflammatory agent (NSAID) to a subject in need thereof to thereby treat myopia are provided. In one embodiment, the method for treating myopia further comprises administering an effective amount anti-muscarinic agent.

Methods for reducing one or more ocular chondrogenic proteins, comprising administering an effective amount of one or more anti-chondrogenesis agents to a subject in need thereof to reduce one or more ocular chondrogenic proteins are also provided herein.

Methods for reducing scleral chondrogenesis, comprising administering an effective amount of one or more anti-chondrogenesis agents to a subject in need thereof to reduce scleral chondrogenesis are also provided herein.

Methods for reducing inflammation induced chondrogenesis, comprising administering an effective amount of one or more anti-chondrogenesis agents to a subject in need thereof to reduce inflammation induced chondrogenesis in the subject are also provided herein.

The invention will become more apparent when read with the accompanying figures and detailed description which follow.

DETAILED DESCRIPTION

Definitions

Figure 1:
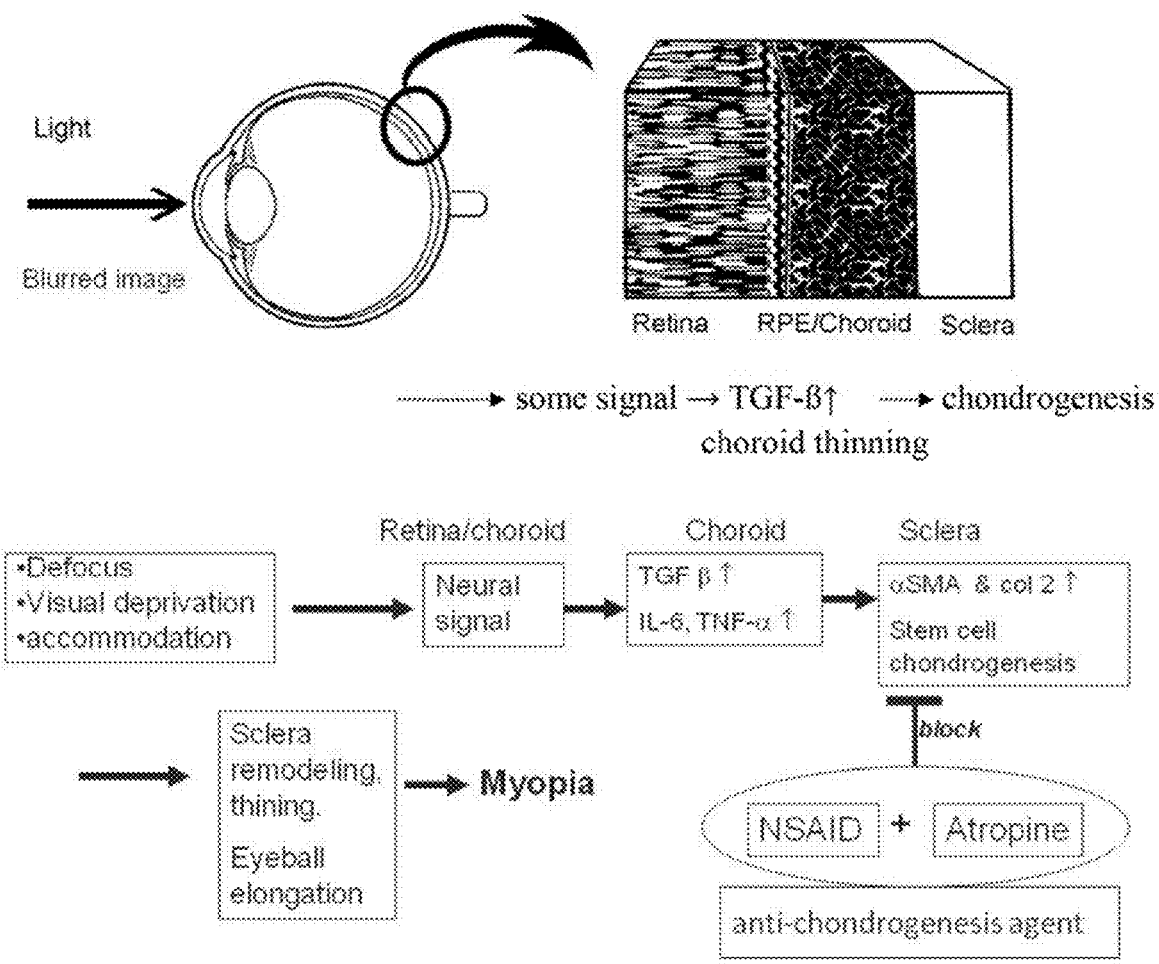
FIG. 1 illustrates schematically a mechanism for myopia.

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of an anti-chondrogenesis agent that is sufficient to treat or ameliorate at least one symptom of myopia, or to reduce one or more ocular chondrogenic proteins, scleral chondrogenesis or inflammation induced chondrogenesis.

The term "treating," "treated," or "treatment" as used herein refers to palliative uses or results, and/or slowing or inhibiting the advancement of myopia progression and/or myopia shift index.

The term "reducing" or "reduce" includes slowing the formation of ocular chondrogenic protein, scleral chondrogenesis, inflammation induced chondrogenesis or myopia progression, or myopia shift, or disassembling the ocular chondrogenic proteins that have already been formed.

Pharmaceutically acceptable salts of the therapeutic agent of the invention include salts derived from an appropriate base, such as an alkali metal (for example, sodium, and potassium), an alkaline earth metal (for example, calcium, and magnesium), ammonium and $NX_4^+$ (wherein X is $C_1$-$C_4$ alkyl). Pharmaceutically acceptable salts of an amino group include salts of organic carboxylic acids, such as tartaric, aliphatic, cycloaliphatic, aromatic, heterocyclic, carboxylic and sulfonic classes of organic acids, such as, for example, formic, glucuronic, malic, maleic, fumaric, pyruvic, aspartic, glutamic, benzoic, anthranilic, mesylic, salicylic, hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, hydroxybutyric, cyclochexylaminosulfonic, galactaric and galacturonic acid and the like, lactobionic, fumaric, and succinic acids; organic sulfonic acids, such as methaniesulfolic, ethanesulfonic, isothionic, benzenylesulfonic and p-toluenesulfonic acids; and inorganic acids such as hydrochloric, hydrobromic, hydroiodic, nitric, carbonic, sulfuric, sulfamic and phosphoric acid and the like. Pharmaceutically acceptable salts of a compound having a hydroxy group consist of the anion of said compound in combination with a suitable cation such as $Na^+$, $NH_4^+$ or $NX_4^+$ (wherein X is, for example, a $C_1$-$C_4$ alkyl group), $Ca^{++}$, $Li^+$, $Mg^{++}$, or, $K^+$ and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound in free form.

The term "myopia" as used herein refers to a condition associated with a refractive error of one or more eyes, wherein light rays entering the eye to focus in front of the retina rather than directly on the retina. The term "myopia" as used herein, encompasses a variety of levels (mild myopia, from 0 to −3 diopters; moderate myopia, from −3 to −5 diopters; and high myopia, from −5 or lower), and types and subtypes of myopia of various etiologies and causes, either known or unknown, including, but not limited to, simple myopia, degenerative myopia, and form deprivation myopia.

The term "diopter" as used herein includes measurement of how much a corrective lens must bend light to focus the light on the retina to normalize the vision. A lens that can bend parallel light rays to a focal point of 1 meter is said to have a power of 1 diopter (1.00 D). A 2-diopters lens can focus light rays at a point 0.5 meters away from itself.

The term "subject" as used herein typically refers to a human or an animal subjected to the methods described herein. It is to be understood that a subject can be a patient with known or suspected myopia disorder, but subjects without known or suspected myopia disorder, such as research subjects, are also included within the scope of the term "subject."

All numbers herein may be understood as modified by "about."

Pharmaceutical Composition

Pharmaceutical compositions for treating myopia, reducing ocular chondrogenic protein, reducing scleral chondrogenesis or reducing inflammation induced chondrogenesis are provided herein. The pharmaceutical compositions comprising a combination of two anti-chondrogenesis agents preferably by advantageous synergistic effects of the combinations.

An anti-chondrogenesis agent is any agent which reduces or slows the process of chondrogenesis. In one embodiment, an anti-chondrogenesis agent in the pharmaceutical composition is a NSAID. In another embodiment, an anti-chondrogenesis agent in the pharmaceutical composition is an anti-muscarinic agent. Non limiting examples of anti-chondrogenesis agent include a microRNA that regulates the expression of lymphoid enhancer-binding factor-1, such as miR-449a (SEQ ID NO.1, see S Paik, et al., miR-449a regulates the chondrogenesis of human mesenchymal stem cells through direct targeting of lymphoid enhancer-binding factor-1, Stem Cells Dev; 21(18):3298-308, 2012), a histone deacetylase inhibitor such as valproic acid (F H Paradis et al., Exposure to valproic acid inhibits chondrogenesis and osteogenesis in mid-organogenesis mouse limbs, Toxicol Sci; 131(1):234-41, 2013), Nicotine (Y Deng et al., Nicotine-induced retardation of chondrogenesis through down-regulation of IGF-1 signaling pathway to inhibit matrix synthesis of growth plate chondrocytes in fetal rats, Toxicol Appl Pharmacol; 269(1):25-33, 2013), bFGF (SEQ ID NO.2) or parathyroid hormone-like peptide (SEQ ID NO.3, S Weiss et al., Impact of growth factors and PTHrP on early and late chondrogenic differentiation of human mesenchymal stem cells, J Cell Physiol; 223(1):84-93, 2010, an agent restricting Leucine (MS Kim, Leucine restriction inhibits chondrocyte proliferation and differentiation through mechanisms both dependent and independent of mTOR signaling, Am J Physiol Endocrinol Metab; 296(6):E1374-82, 2009), 17beta-Estradiol (S. Fushimi et al., 17beta-Estradiol inhibits chondrogenesis in the skull development of zebrafish embryos, Aquat Toxicol; 95(4):292-8, 2009), versican (Y Yang et a., The G3 domain of versican inhibits mesenchymal chondrogenesis via the epidermal growth factor-like motifs, J Biol Chem; 273(49):33054-63, 1998), SB203580 (a specific inhibitor of p38MAPK, D Kim et al., Alterations in the temporal expression and function of cadherin-7 inhibit cell migration and condensation during chondrogenesis of chick limb mesenchymal cells in vitro, J Cell Physiol; 221(1):161-70, 2009), LiCl (an inhibitor of GSK-3beta, D Kim et al., 2009) or the like.

In one exemplary embodiment, the pharmaceutical composition includes at least one NSAID and at least one anti-muscarinic agent.

In certain embodiments, NSAIDs for use in the present invention may be non-selective cyclooxygenase (COX) inhibitors, its derivatives, salts and structural analogues, i.e., compounds that inhibit both COX-1 and COX-2 proteins. Non limiting examples of non-selective COX inhibitors include salicylic acid derivatives (e.g., aspirin, sodium salicylate, choline magnesium trisalicylate, salsalate, diflunisal, sulfasalazine and olsalazine), indole and indene acetic acids (e.g., indomethacin and sulindac), heteroaryl acetic acids (e.g., tolmetin, diclofenac and ketorolac), arylpropionic acids (e.g., ibuprofen, naproxen, flurbiprofen, ketoprofen, fenoprofen, and oxaprozin), anthranilic acids (fenamates) (e.g., mefenamic acid and meclosfenamic acid), enolic acids (e.g., the oxicams, piroxicam and meloxicam) and alkanones (e.g., nabumetone).

In certain embodiments, NSAIDs for use in the present invention may be selective COX-2 inhibitors, its derivatives, salts and structural analogues. Non limiting examples of selective COX—of selective COX-2 inhibitor include diaryl-substituted furanones (e.g., rofecoxib), diaryl-substituted pyrazoles (e.g., celecoxib), indole acetic acids (e.g., etodolac) and sulfonanilides (e.g., nimesulide). Further examples of selective COX-2 inhibitor are disclosed in U.S. Pat. No. 6,440,963 and WO 2004/054560, which are incorporated by reference in its entirety.

Preferred NSAIDs for use in the invention include, but are not limited to, Ketorolac, Diclofenac, Indomethacin, Bromfenac, Nepafenac and Flurbiprofen.

Examples of anti-muscarinic agent include, but are not limited to, Atropine, Homatropine, Scopolamine, its derivatives, salts, and structural analogues.

Anti-muscarinic agents may cause side effects of blurred vision and photophobia. These side effects maybe overcome by administering lower dosage of anti-muscarinic agents, in combination with one or more anti-chondrogenesis agent, to achieve the desired therapeutic effect. The observed synergistic effect of a pharmaceutical composition comprising a combination of an anti-muscarinic agent (e.g. atropine) and an NSAID (e.g. ketorolac) may afford effective treatment of myopia wherein one or even all of the lower dosages of the anti-chondrogenesis agents would not be sufficient to have a therapeutic effect when the respective anti-chondrogenesis agent is used in monotherapy.

The pharmaceutical compositions to be administered according to the methods of some embodiments provided herein can be readily formulated with, prepared with, or administered with, a pharmaceutically acceptable carrier. Such preparations may be prepared by various techniques. Such techniques include bringing into association active components (such as NSAID or anti-muscarinic agent) of the pharmaceutical compositions and an appropriate carrier. In one embodiment, pharmaceutical compositions are prepared by bringing into association active components of the pharmaceutical compositions with liquid carriers, with solid carriers, or with both.

The pharmaceutical compositions are administered in an aqueous suspension, an oil emulsion, water in oil emulsion and water-in-oil-in-water emulsion, and in carriers including, but not limited to, creams, gels, liposomes (neutral, anionic or cationic), lipid nanospheres or microspheres, neutral, anionic or cationic polymeric nanoparticles or microparticles, site-specific emulsions, long-residence emulsions, sticky-emulsions, micro-emulsions, nano-emulsions, microspheres, nanospheres, nanoparticles and minipumps, and with various natural or synthetic polymers that allow for sustained release of the pharmaceutical composition including anionic, neutral or cationic polysaccharides and anionic, neutral cationic polymers or copolymers, the minipumps or polymers being implanted in the vicinity of where composition delivery is required.

The pharmaceutical compositions provided herein may optionally include anti-oxidants, buffers, bacteriostatic agents, suspending agents thickening agents, preservatives, co-solvents and viscosity building agents or other therapeutic ingredients. The carrier and other therapeutic ingredients must be acceptable in the sense of being compatible with the other ingredients of the composition and not deleterious to the recipient thereof. Suitable preservatives for ophthalmic preparations include: benzalkonium chloride, thimerosal, chlorobutanol, methyl paraben, propyl paraben, phenylethyl alcohol, edetate disodium, sorbic acid, Onamer M, or other agents known to those skilled in the art. In one embodiment, the preservative is employed at a level of from 0.004% to 0.02%.

For administration in a non-aqueous carrier, active components of the pharmaceutical compositions provided herein are emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid is suspended in the neutral oil. A suitable phospholipid is, but is not limited to, phosphatidylserine, which targets receptors on macrophages. The pharmaceutical compositions provided herein are optionally formulated in aqueous media or as emulsions using known techniques.

The pharmaceutical compositions are administered in an amount effective to reduce ocular chondrogenic protein, reduce scleral chondrogenesis, reduce inflammation induced chondrogenesis or to induce a therapeutic response in an animal, including a human with myopia. The dosage of the pharmaceutical composition administered will depend on the severity of the condition being treated, the particular formulation, and other clinical factors such as weight and the general condition of the recipient and route of administration. In one exemplary embodiment, the amount of the pharmaceutical composition administered corresponds to about 0.001% to about 1% by weight atropine. In another exemplary embodiment, the amount of the pharmaceutical composition administered corresponds to about 0.005%, 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1% by weight atropine, or any % in between 0.001% and 1% in 0.001% increments. In another exemplary embodiment, the amount of the pharmaceutical composition administered corresponds to about 0.05% to about 1% by weight Ketorolac. In another exemplary embodiment, the amount of the pharmaceutical composition administered corresponds to about 0.1%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95% by weight Ketorolac, or any % in between in 0.01% increments. In another exemplary embodiment, the amount of the pharmaceutical composition administered corresponds to about 0.5% by weight Ketorolac. In another exemplary embodiment, the amount of the pharmaceutical composition administered corresponds to from about 0.01%, 0.025%, 0.05%, 0.1%, 0.15% to about 0.2% of Diclofenac by weight or any % in between in 0.01% increments. Useful dosages of the pharmaceutical compositions provided herein are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

In accordance with the methods provided herein, the pharmaceutical composition is delivered by any of a variety of routes including, but not limited to, injection (e.g., subcutaneous, intramuscular, intravenous, intra-arterial, intraperitoneal, intradermal, intravitreal); cutaneously; dermally; transdermal; oral (e.g., tablet, pill, liquid medicine, edible film strip); implanted osmotic pumps; suppository, aerosol spray, topical, intra-articular, ocular, nasal inhalation, pulmonary inhalation, impression into skin and electroporation. In one embodiment, the pharmaceutical composition of the present invention can be administered as solution in a suitable ophthalmic vehicle.

In forming the pharmaceutical compositions for topical ocular administration, the combination comprises 0.001% to about 0.005% by weight atropine and 0.1% to about 0.5% by weight Ketorolac solution in water at pH of 4.5 to 8.0, e.g. about 6.9. It is recommended that the solution be topically applied by placing one drop in the affected eye once a day.

The pharmaceutical composition may be administered in a single dose treatment or in multiple dose treatments, over a period of time appropriate to the condition being treated. The pharmaceutical composition may conveniently be administered at appropriate intervals, for example, once a day, twice a day, three times a day, once every second day, once every three days or once every week, over a period of at least 3 months, at least 1 year, or until the symptoms and signs of myopia resolved.

Methods for Reducing Scleral Chondrogenesis

Down regulation of ocular chondrogenic proteins and/or ocular inflammation markers reduces scleral chondrogenesis.

In one embodiment, the use of an effective amount of one or more anti-chondrogenesis agents or a pharmaceutical composition described herein may alter or reduce the amount of one or more ocular chondrogenic proteins in a subject in need thereof.

One example of ocular chondrogenic protein is TGF-$\beta$. In one embodiment, the TGF-$\beta$ protein is selected from the group consisting of TGF-$\beta$1 (SEQ ID NO:4), TGF-$\beta$2 (SEQ ID NO:5) and TGF-$\beta$3 (SEQ ID NO:6), all of which are located predominately in the choroid. Another example of ocular chondrogenic protein is $\alpha$-SMA (SEQ ID NO:7). Another example of ocular chondrogenic protein is Col2 (SEQ ID NO:8). Both $\alpha$-SMA and Col2 are located predominately in the sclera.

In another embodiment, the present invention provides the use of an effective amount of one or more anti-chondrogenesis agents or a pharmaceutical composition described herein for reducing inflammation induced chondrogenesis in a subject in need thereof. The inflammation markers responsible for inducing scleral chondrogenesis include, but are not limited to, IL-6 and TNF-$\alpha$.

In yet another embodiment, the present invention provides the use of an effective amount of one or more anti-chondrogenesis agents or a pharmaceutical composition described herein for reducing scleral chondrogenesis in a subject in need thereof.

The anti-chondrogenesis agent maybe administered concomitantly or non-concomitantly.

Methods for Treating or Reducing the Severity of Myopia

Without being bound by any particular theory, it was believed that the expression profiles of ocular inflammation markers and ocular chondrogenic proteins, such as TGF-$\beta$, $\alpha$-SMA and Col2, are correlated with scleral chondrogenesis and myopia. FIG. 1, for example and without limitation, illustrates a mechanism for the development of myopia, wherein increase levels of TGF-$\beta$s and inflammatory markers (such as IL-6 and TNF-$\alpha$) in the choroid lead to the formation of $\alpha$-SMA and Col2 in the sclera and scleral chondrogenesis. The sclera then undergo remodeling and elongation, followed by the development of myopia.

The present invention provides methods for treating or reducing the severity of myopia, by administering one or more anti-chondrogenesis agents in an effective amount or the pharmaceutical composition described herein to a myopic subject in need of myopia treatment. The anti-chondrogenesis agent may be administered concomitantly or non-concomitantly. The methods also encompass research methods and uses, including in vitro and in vivo methods of treating, or inhibiting the progression of myopia in the subject.

In one embodiment, the method for treating myopia comprises identifying a myopic subject who exhibits side effect to anti-muscarinic agent, and treating said subject with an effective amount of NSAID, without the anti-muscarinic agent or with a lower dose of anti-muscarinic agent (e.g. 0.05% of atropine).

Embodiments of the present invention are illustrated by the following examples, which are not to be construed in any way as imposing limitations upon the scope thereof. During the studies described in the following examples, conventional procedures were followed, unless otherwise stated. Some of the procedures are described below for illustrative purpose.

Description of Materials and Methods Used in the Examples

Mice: Male wild type C57BL/6 mice (Jackson Labs) were used in the examples. All procedures were performed in accordance with an institutional IACUC approved protocol as well as the ARVO Statement for the Use of Animals in Ophthalmic and Vision Research.

Scleral Stem/Progenitor Cells (SSPCs) Isolation and Culture:

The SSPCs were isolated and cultured as previously described by CL Tsai et al. (Identification of multipotent stem/progenitor cells in murine sclera. *Invest Ophthalmol Vis Sci* 52:5481-5487, 2011). In brief, sclera from the mouse was obtained and was carefully dissected away from limbus and optic disc under a dissection microscope. After retina and choroid tissues were removed, the scleral tissue was cut into small pieces and digested with 1.5 mg/ml collagenase type I (Worthington Biochemical, Lakewood, USA) and 2 mg/ml of dispase (Roche, Basel, Switzerland) in PBS for 1 h at 37° C. to release individual cells. Individual cells were cultured in $\alpha$-MEM (Invitrogen, Carlsbad, USA), supplemented with 20% lot-selected FBS (Equitech-Bio, Kerrville, USA), glutamine, penicillin/streptomycin and 100 mM 2-mercaptoethanol (Invitrogen) for 8 to 10 days at 5% $CO_2$, 37° C.

TGF-$\beta$ Treatment:

Different concentrations of TGF-$\beta$2 were added into 12-wells of SSPCs. After 24 hrs, the images of SSPC morphology were recorded. The total RNA was extracted for further analysis. A chamber slide culture for the immunofluorescence study was performed under the same condition.

Induction of Chondrogenic Differentiation.

At semiconfluence, SSPCs were trypsinized and counted to make aliquots of $2\times10^5$ cells in 2 ml growth medium which were spun down at 500 g for 10 min to obtain the pellet. The pellets were incubated at 37° C., under 5% $CO_2$. Within 12-24 h of incubation, the cells formed an essentially spherical aggregate that did not adhere to the walls of the tube. Culture medium was added with 10 ng/ml TGF-$\beta$2 and the medium was changed at 2 to 3 day intervals. The pellets were then harvested at 4 weeks. Subsequently, they were washed twice in PBS, fixed in 4% paraformaldehyde for 3 h at room temperature and prepared for paraffin embedment. Eight μm thick sections were obtained for immunohistochemistry, Immunohistochemistry and Immunofluorescence Study:

Immunohistochemistry and immunofluorescence studies were performed to demonstrate the presence of α-SMA protein and Col2 during chondrogenesis. For immunohistochemistry, paraffin sections were treated with a 20% blocking goat serum for 30 min, then incubated with primary antibodies which were rabbit IgG anti-SMA mAb at 1:200 dilution (Abcam, Temecula, Calif.) and mouse IgG2a anti-type II collagen mAbb at 1:100 dilution (Abcam, Temecula, Calif.) at 4° C. overnight. The sections were then treated with horseradish peroxidase (HRP)-conjugated secondary antibodies at 1:200 (Santa Cruz Biotechnology, Santa Cruz, Calif.) for 1 hour. The DAB reagent (diaminobenzidine tetrahydrochloride) was subsequently used to detect the immunoactivity. For immunofluorescence, cryostat sections and rehydrated paraffin sections were treated with blocking serum, incubated with primary antibody, reacted with the corresponding fluorescein-isothiocyanate-conjugated secondary antibody, and finally evaluated by fluorescence microscopy.

Real Time PCR:

Total RNA from SSPCs or the choroid tissue in each eye was isolated using Trizol (Invitrogen, Carlsbad, Calif.) accordingly to the manufacture's protocol. qRT-PCR analysis was carried out using the iScript one-step RT-PCR kit with SYBR Green (Bio-Rad, Hercules, USA) on an ABI PRISM 7900 HT sequence detection system (Applied Biosystems, Foster City, USA), according to the manufacturer's instructions. Primers used for the experiment were: α-SMA (Forward primer/SEQ ID NO:9: 5'-ATGCCTCTGGACGTACAACTG-3', Reverse primer/SEQ ID NO:10 5'-CGGCAGTAGTCACGAAGGAAT-3'), Col2 (Forward primer/SEQ ID NO:11 5'-GTCCTTCTGGCCCTAGAGGT-3', Reverse primer/SEQ ID NO: 12 5'-TGTTTCTCCTGAGCGTCCA-3'), β-actin (Forward primer/SEQ ID NO:13 5'-CATTGCTGACAG-GATGCAGA-3', Reverse primer/SEQ ID NO:14 5'-CT-GATCCACATCTGCTGGAA-3'), and glyceraldehyde 3-phosphate dehydrogenase (GAPDH) (Forward primer/SEQ ID NO:15 5'-AACTTTGGCATTGTGGAAGG-3', Reverse primer/SEQ ID NO:16 5'-ACACAT-TGGGGGTAGGAACA-3'). GAPDH and β-actin served as controls. Ct values of the control gene were subtracted from those of α-SMA and Col2 to provide a semiquantitative analysis, and fold change relative to no treatment was assessed.

Deprived Myopia of Mice.

On the day of the experiment (postnatal day [P] 21~24), C57BL/6J mice were anesthetized by intraperitoneal injection of ketamine (90 mg/kg) and xylazine (10 mg/kg), and the diffuser eye patches were sutured to the skin around the right eye whereas the left eye served as a control. The hemispherical plastic diffuser eye patches were made from caps of 0.5-mL PCR plastic tubes. The mice were recovered and monitored on a warming pad until they were fully mobile. Deprived myopia mice were housed in transparent plastic cages under 12 hours of light (200±15 lux horizontal illuminance) and 12 hours of darkness for 21 days. A spectral-domain optical coherence tomography was used for ocular biometric measurement before and after form-deprived myopia induction.

Western Blot Analysis:

The total protein from the sclera was extract by using RIPA protein extraction buffer. After homogenization of scleral tissue, the sample was centrifuged and the supernatant was collected. The protein concentration of each sample was measured using a BCA™ protein Assay Kit (Bio-Rad). Scleral protein samples were standardized and electrophoresed on 10% SDS-PAGE gel, then transferred to a polyvinylidene fluoride transfer membrane (Immun-Blot PVDF Membrane, BIO-RAD) at 21 V for 1 h. Membranes were blocked for 1 h at room temperature with 5% dry milk in PBS with 0.1% Tween and incubated at 4° C. overnight with primary antibodies. Membranes were washed and incubated with 1:10,000 goat anti-mouse or anti-rabbit IgG antibodies conjugated to horseradish peroxidase (Santa Cruz) for 1 h at room temperature and washed again. Membranes were developed by chemiluminescence with the reagent Lumigen TMA-6 (GE Healthcare UK limited, Buckinghumshire, UK) and images were captured with the LAS-4000 imaging system (Fujifilm, Tokyo, Japan). Protein bands were quantified using ImageJ software.

Statistical Analysis:

For in vitro studies, the statistical significant was calculated by ANOVA test with Bonferroni post hoc test. For in vivo studies, the statistical significance was calculated by analysis of variance (the paired t-test). Statistical significance was defined as a p value less than 0.05.

EXAMPLES

Example 1: SSPC Morphology Change after TGF-β Treatment

An in vitro study of the SSPC morphology change after TGF-β treatment was performed. SSPC was incubated with TGF-β2 treatment (0.1-10 ng/ml) for 24 hrs as previously described. Microscopy study shows without TGF-β2 treatment or at a low concentration of TGF-β2 treatment (0.1 ng/ml), many SSPCs had thin spindle shape and showed a widened phenotype. In addition, the cytoskeleton filaments of SSPCs were not prominent. After exposing to a higher concentration of TGF-β2 (1 to 10 ng/ml), SSPCs became broad with prominent cytoskeletal filaments. Immunofluorescence microscopy showed an increased number of α-SMA positive SSPCs (with prominent intracellular α-SMA filament staining) after treatment with 10 ng/ml of TGF-β2.

Example 2: Effect of TGF-β Treatment on α-SMA and Col2 Expression

An in vitro study of the effect of TGF-β treatment on α-SMA and Col2 expression was performed using SSPC and 3-D pellets of SSPCs. SSPCs and 3-D pellets of SSPC were treated with various concentrations of TGF-β2, as previously described.

Figure 2:
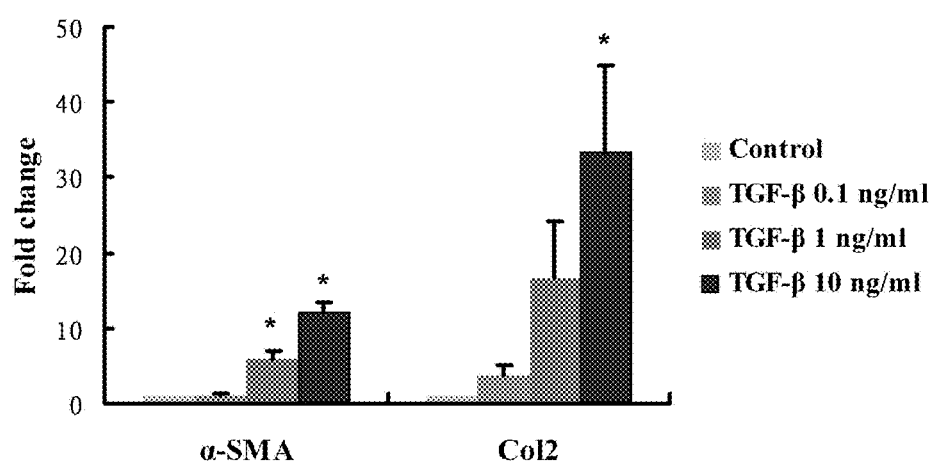
FIG. 2 is bar graph illustrating the levels of alpha smooth muscle actin ($\alpha$-SMA) and collagen type 2 (Col2) mRNA normalized to $\beta$-actin expression in scleral stem/progenitor cells (SSPCs) with or without Transforming growth factor beta (TGF-$\beta$) treatment. Data are expressed as fold change over the control sample as determined by the delta-delta Ct method. Bars, SD. * represents statistically significant.

Total mRNA was analyzed to determine whether there was any alteration in α-SMA and Col2 gene expression after 0.1 to 10 ng/ml of TGF-β2 treatment for 24 hrs. FIG. 2 shows there is a statistically significant increase in α-SMA and Col2 gene expressions after TGF-β2 treatment using quantitative Real Time-PCR analysis, in a dose dependent manner ($p<0.0001$ and $=0.011$ respectively).

SSPC pellets were cultured in control medium and medium containing 10 ng/ml of TGF-β2 (TM-pellets) for 4 weeks. Histological analysis showed that most SSPC were located in the midperipheral and peripheral area which surrounded the central matrix tissue in TM-pellets. Immunohistochemical analysis showed Col2 was expressed in the local, mid-peripheral area of TM-pellets whereas α-SMA expression was more extensive within the TM-pellets, especially in mid-peripheral area and peripheral area. In contrast, Col2 and α-SMA expressions were less in the control group.

Example 3: The Expression of Col2 and α-SMA in Sclera of FDM Mice

An in vivo study evaluating the expression of Col2 and α-SMA in the sclera was evaluated using FDM Mice. FDM was induced in the right eye of the mouse as described previously and the left eye served as a control. The differences between the two eyes of each mouse in axial length was not significant at the beginning (p=0.378). By Day 21, form deprived eyes had myopia with an axial length of 3055±39 μm which was significantly longer than the contralateral control eyes (3015±40 μm, p<0.001)

Figure 3:
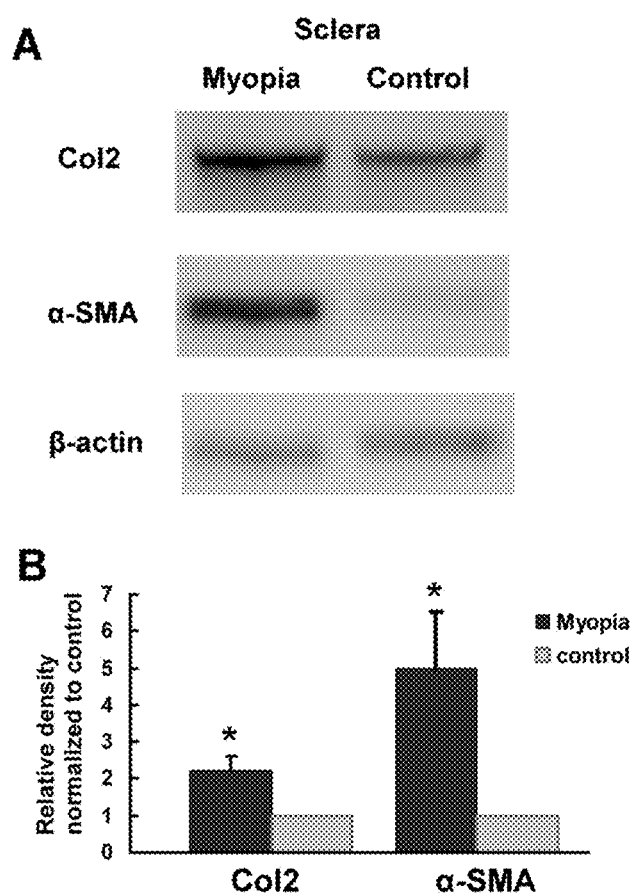
FIG. 3 is an assembly of images illustrating the expression of $\alpha$-SMA and Col2 in the sclera of mice with form-deprivation myopia (FDM). Panel A is a photograph of a western blot showing the scleral Col2 and $\alpha$-SMA expression levels were increased in FDM eyes. Panel B is a bar graph of densitometry analysis showing the levels of scleral Col2 and scleral $\alpha$-SMA in FDM eyes are significantly higher than that of the control eyes.

FIG. 3 shows after 21 days of visual deprivation, the expressions of Col2 and α-SMA were higher in the sclera of FDM eyes using western blot analysis. FIGS. 3A and 3B show the expressions of Col2 and α-SMA in FDM eyes were significantly higher than contralateral control eyes in the same mouse (P=0.021 for Col2 and (p=0.042 for α-SMA). Immunostaining shows Col2 expression was higher in the scleral region of the FDM eyes than in the control eyes, whereas α-SMA expression was greater in the scleral (close to the choroid side) and choroid areas of FDM eyes in comparison to control eyes.

Example 4: The Expression of TGF-β mRNA Levels in the Choroid of FDM Mice

An in vivo study evaluating the expression of TGF-β in the choroid was performed using FDM Mice. FDM was induced in mice as previously described.

Figure 4:
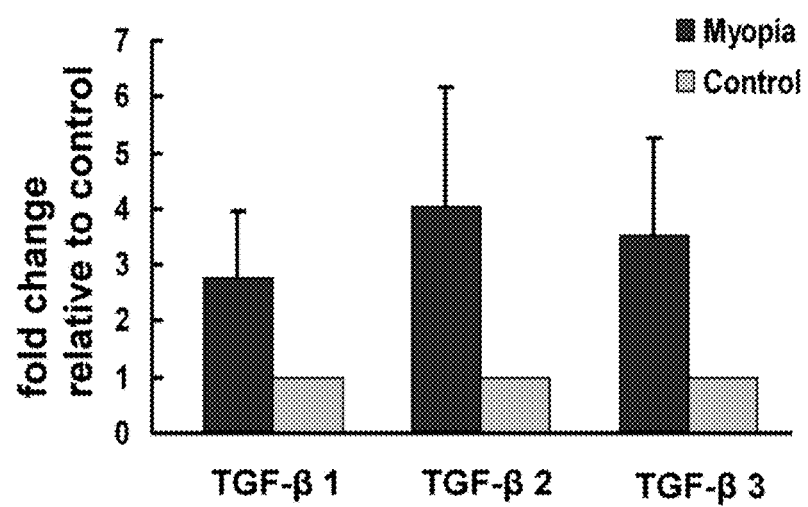
FIG. 4 is a bar graph showing the levels of TGF-$\beta$1, TGF-$\beta$2 and TGF-$\beta$3 mRNA expression in the RPE-choroid complex of the FDM eyes were significantly higher than that of the control eyes.

The relative expressions of TGF-β1, TGF-β2 and TGF-β3 mRNA in the choroids of FDM mice were significantly higher than contralateral control choroids (2.98, 4.44 and 3.86 fold change, p=0.042, 0.045 and 0.041, respectively, FIG. 4).

Example 5: The Effect of Anti-Muscarinic Agent and NSAID on Col2 and α-SMA Expression An in vitro study examining the effect of an anti-muscarinic agent and NSAID on Col2 and α-SMA expressions was performed using human SSPC. SSPCs were treated with 1 mM of atropine, 5 mM of ketorolac and 1 mM of diclofenac in the presence of TGF-β2 (10 ng/ml), as previously described.

Figure 5A:
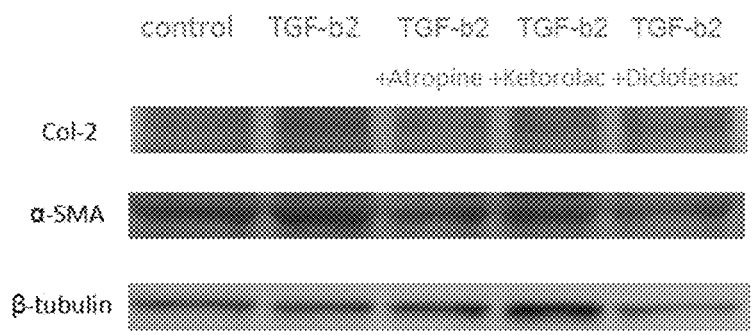
FIG. 5A (a western blot analysis) and FIG. 5B (a bar graph) illustrate the expression profiles of Col2 and $\alpha$-SMA in human SSPC treated with 10 ng/ml TGF-$\beta$2, with or without Atropine, Ketorolac and Diclofenac.
Figure 5B:
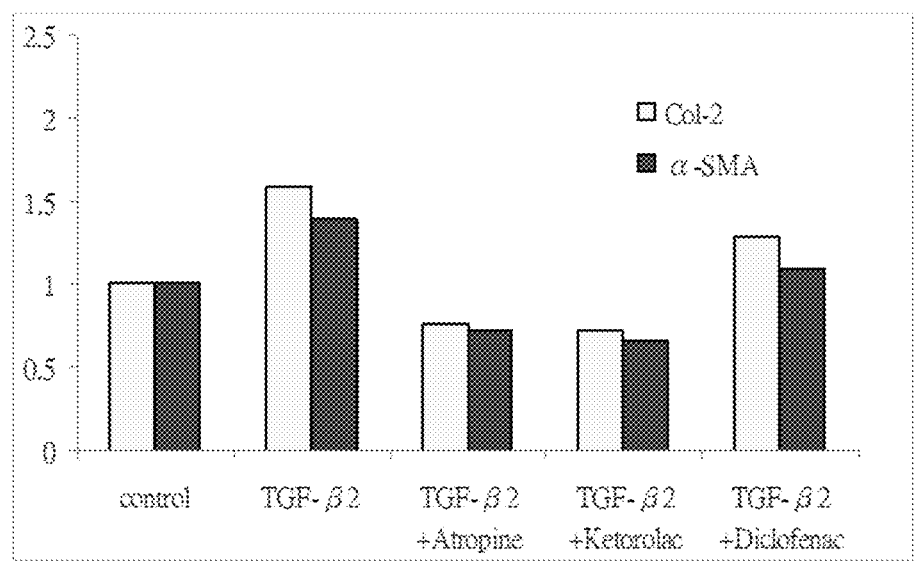

FIGS. 5A and 5B show the expressions of Col2 and α-SMA were suppressed by atropine, ketorolac and diclofenac, in the presence of TGF-β2.

Example 6: Treating Myopia Subjects with a Pharmaceutical Composition Comprising Anti-Muscarinic Agent and NSAID A clinical study of 11 myopia patients using atropine and a pharmaceutical composition comprising atropine and ketorolac was conducted.

11 myopic patients received atropine treatment for at least a year, with the dose of atropine ranged from 0.005% to 1% weight atropine per unit dose (about 0.05 to 0.5 ml). Each affected eye was given one drop (about 0.05 to 0.5 ml) of atropine ophthalmic solution at night. During the atropine treatment, the average myopia progression rate for these 11 myopic patients was −0.9 Diopter/year.

Figure 6:
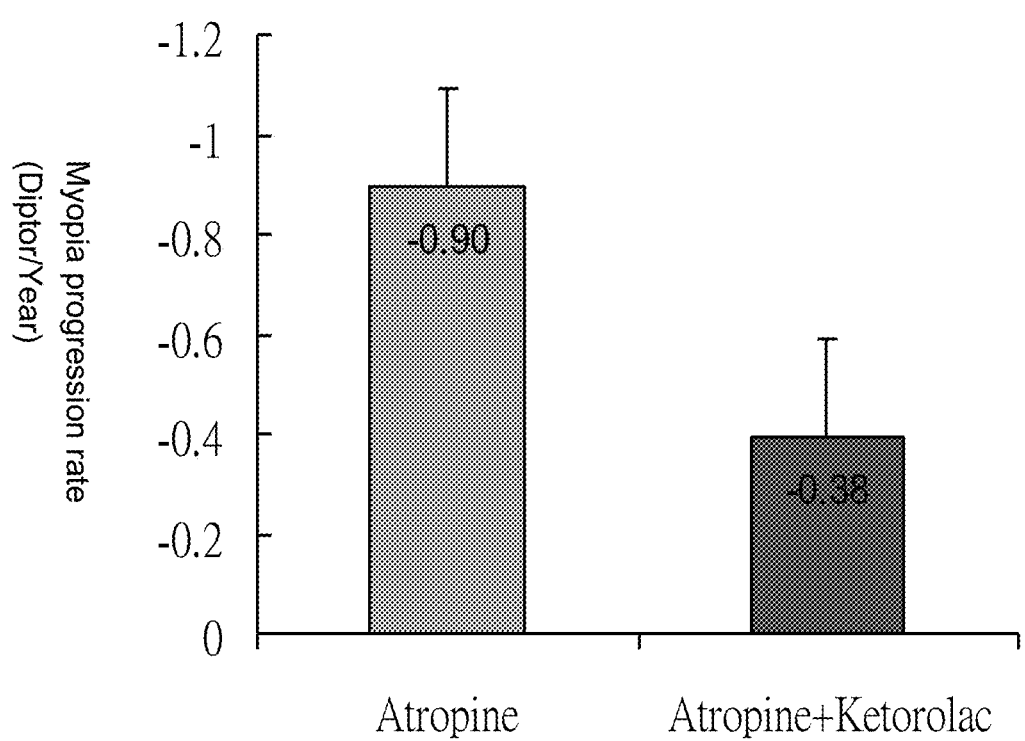
FIG. 6 is a bar graph illustrating the myopia progression rate (Diopter per year) in 11 myopia subjects treated with atropine eye drops and the combined atropine and ketolorac eye drops.

Subsequently, these 11 myopic patients received a pharmaceutical composition comprising atropine and ketorolac for at least 3 months. The dose of atropine ranged from about 0.005% to about 1% weight atropine per unit dose (about 0.05 to 0.5 ml) and the dose of ketorolac ranged from about 0.25% to about 0.5% weight ketorolac per unit dose (0.5 ml). Each affected eye was given one drop (about 0.05 to 0.5 ml) of combined atropine with ketorolac ophthalmic solution at night. During the combined atropine with ketorolac treatment, the average myopia progression rate for these 11 myopia patients reduced to −0.38 Diopter/year (FIG. 6).

Example 7: Treating a Myopia Subject with NSAID

A myopic patient could not tolerate the side effects of atropine and was given NSAID to treat his myopia. The dose of ketorolac was about 0.5% weight ketorolac per unit dose (about 0.05 to 0.5 ml) and the affected eye was given one drop (about 0.05 to 0.5 ml) of ketorolac ophthalmic solution at night.

Figure 7:
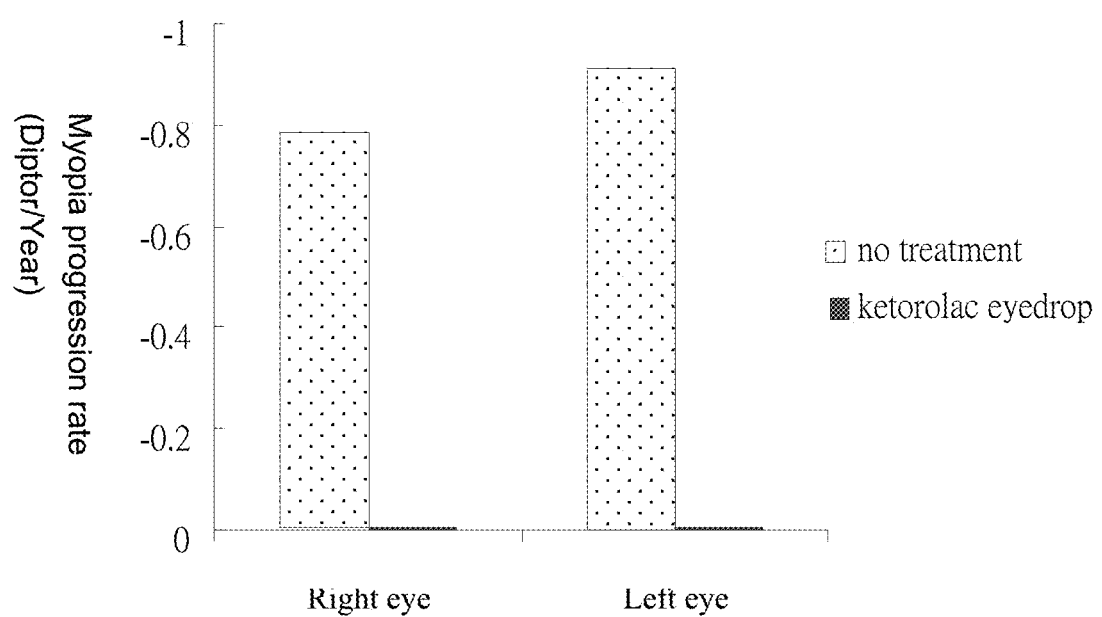
FIG. 7 is a bar graph illustrating the myopia progression rate of a myopia subject without any treatment, followed by 3 months of ketolorac treatment.

The average myopia progression rate for this patient was −0.78 Dioptor per year in right eye and −0.91 Diopter per year in left eye without any treatment. After three months of NSAID treatment, there was no myopia progression in both eyes (FIG. 7).

Example 8: The Expression of Inflammation Markers in Choroids of FDM Mice

An in vivo study evaluating the expression of inflammation markers in the choroid was evaluated using FDM Mice. FDM was induced in the right eye of the mouse as described previously and the left eye served as a control.

Figure 8A:
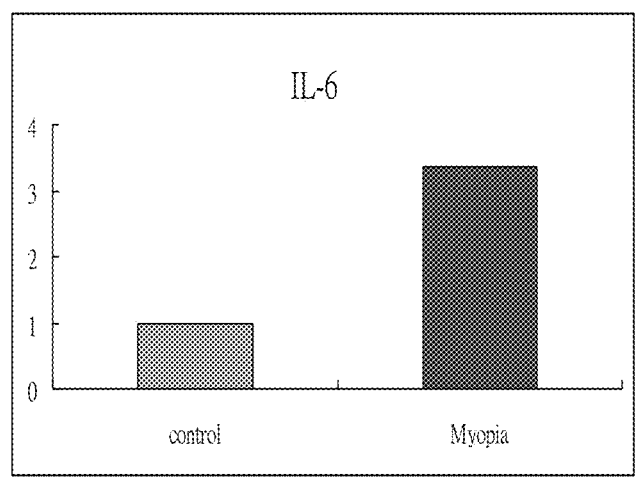
FIG. 8A is a bar graph illustrating the level of interleukin 6 (IL-6) mRNA normalized to GADPH expression in the choroids of form deprivation myopia (FDM) mice is higher than that of control mice.
Figure 8B:
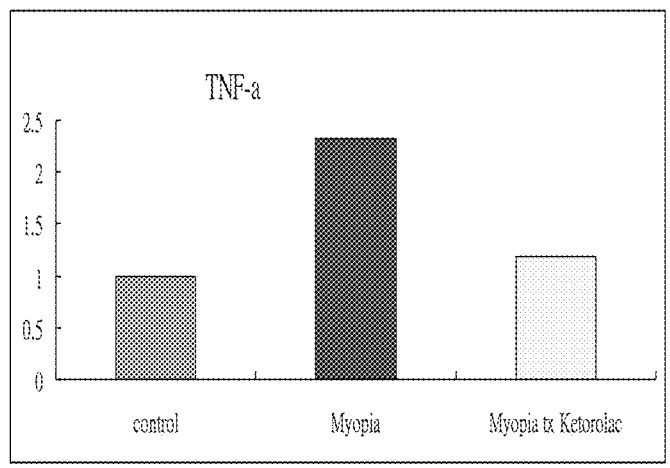
FIG. 8B is a bar graph illustrating the level of tumor necrosis factor-alpha (TNF-$\alpha$) in the choroids is higher in the FDM mice than that of control mice. TNF-$\alpha$ expression is suppressed by ketorolac eye drop.

FIG. 8A shows the level of IL-6 by real-time PCR in the choroids of FDM eye was higher than that of control eye. FIG. 8b shows the level of TNF-α by real-time PCR in the choroids of FDM eye was higher than that of control eye. The level of TNF-α was suppressed by administering one ketorolac eye drop once a day to the FDM eye.

Example 9: Treatment of SSPC with a Pharmaceutical Composition Comprising Atropine and Ketorolac Reduced α-SMA and Col2

An in vitro study of the effect of a pharmaceutical composition comprising Atropine and Ketorolac on α-SMA and Col2 expressions was performed using SSPCs. SSPCs were treated with 10 ng/ml of TGF-β2, as previously described.

Figure 9A:
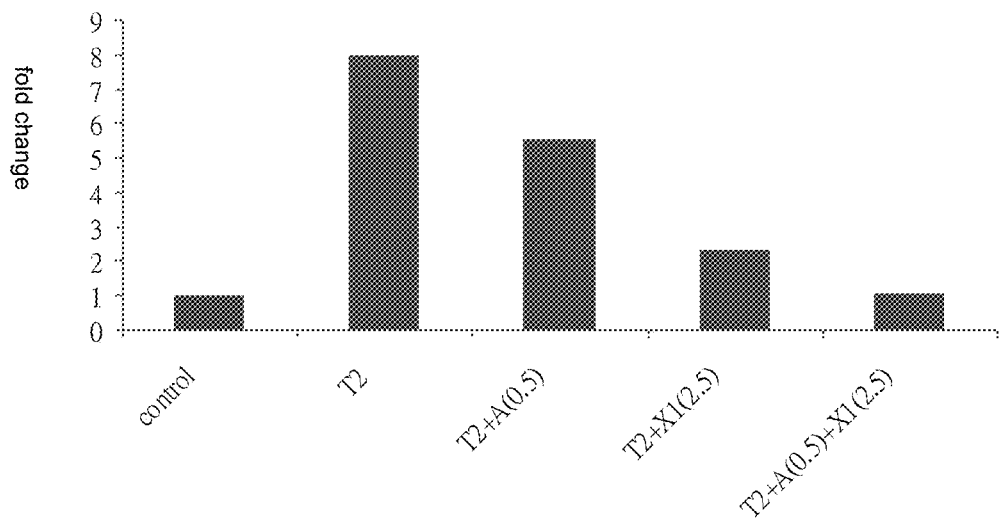
FIG. 9A is a bar graph illustrating the suppressive effect of atropine (A), ketorolac (X1) and a pharmaceutical composition comprising atropine and ketorolac on $\alpha$-SMA expression in SSPC in the presence of TGF-$\beta$2 (T2). The pharmaceutical composition comprising atropine and ketorolac has a synergistic effect on $\alpha$-SMA suppression.

FIG. 9A shows the expression of α-SMA increased in the presence of TGF-β2 (T2) but reduced with 0.5 mM of atropine (A), 2.5 mM of Ketorolac (X1), and a pharmaceutical composition comprising Atropine and Ketorolac, in the presence of TGF-β2.

Figure 9B:
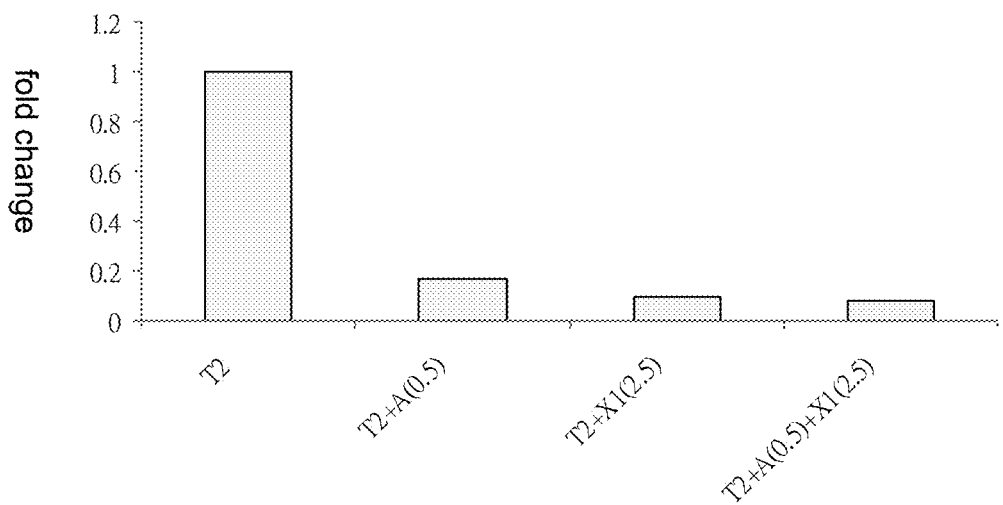
FIG. 9B is a bar graph illustrating the suppressive effect of atropine (A), ketorolac (X1) and a pharmaceutical composition comprising atropine and ketorolac on Col2 expression in SSPC in the presence of TGF-$\beta$2 (T2). The pharmaceutical composition comprising atropine and ketorolac has a synergistic effect on Col2 suppression.

FIG. 9B shows the expression of Col2 increased in the presence of TGF-β2 (T2) but reduced with 0.5 mM of atropine (A), 2.5 mM of Ketorolac (X1), and a pharmaceutical composition comprising Atropine and Ketorolac, in the presence of TGF-β2.

The results show that a pharmaceutical composition comprising Atropine and Ketorolac has a synergistic effect in α-SMA and Col2 reduction.

What is claimed is:

1. A method for treating myopia, comprising the step of administering an effective amount of NSAID to a myopic subject in need thereof.

2. The method of claim 1, wherein the NSAID is selected from Ketorolac, Diclofenac, Indomethacin, Bromfenac, Nepafenac, Flurbiprofen, or combination thereof.

3. The method of claim 2, wherein the NSAID is Ketorolac at a concentration of about 0.05% to about 1% by weight.

4. The method of claim 2, wherein the NSAID is diclofenac at a concentration of about 0.01% to about 0.2% by weight.

5. The method of claim 1, wherein the NSAID is administered topically.

6. A method for treating myopia, comprising the step of administering an effective amount of NSAID and an anti-muscarinic agent to a myopic subject in need thereof.

7. The method of claim 6, wherein the NSAID is selected from Ketorolac, Diclofenac, Indomethacin, Bromfenac, Nepafenac, Flurbiprofen, or combination thereof.

8. The method of claim 7, wherein the NSAID is Ketorolac at a concentration of about 0.05% to about 1% by weight.

9. The method of claim 7, wherein the NSAID is diclofenac at a concentration of about 0.01% to about 0.2% by weight.

10. The method of claim 6, wherein the anti-muscarinic agent is atropine.

11. The method of claim 10, wherein the concentration of atropine is about 0.001% to about 1% by weight.

12. The method of claim 10, wherein the concentration of atropine is about 0.005% to about 0.05% by weight.

13. The method of claim 6, wherein the NSAID and the anti-muscarinic agent are topically administered to the eye.

14. A method for treating myopia, comprising the step of administering a pharmaceutical composition, comprising, in a pharmaceutically acceptable carrier, an effective amount of NSAID to a myopic subject in need thereof.

15. The method of claim 14, wherein the NSAID is selected from Ketorolac, Diclofenac, Indomethacin, Bromfenac, Nepafenac, Flurbiprofen, or combination thereof.

16. The method of claim 15, wherein the pharmaceutical composition further comprises an effective amount of an anti-muscarinic agent.

17. The method of claim 16, wherein the anti-muscarinic agent is atropine.

18. The method of claim 17, wherein the pharmaceutical composition further comprises one or more ingredients chosen from anti-oxidants, buffers, bacteriostatic agents, suspending agents, thickening agents, co-solvents or viscosity building agents.

19. The method of claim 14, wherein the pharmaceutical composition further comprises an effective amount of an anti-muscarinic agent.

20. The method of claim 19, wherein the pharmaceutical composition further comprises one or more ingredients chosen from anti-oxidants, buffers, bacteriostatic agents, suspending agents, thickening agents, co-solvents or viscosity building agents.

\* \* \* \* \*